United States Patent
Hatano et al.

(12)

(10) Patent No.: US 6,379,694 B1
(45) Date of Patent: Apr. 30, 2002

(54) FEED FOR PREVENTION AND/OR TREATMENT OF COCCIDIOSIS

(75) Inventors: Kazuhiro Hatano; Ryuichi Azuma; Nobuyuki Arai, all of Tochigi (JP)

(73) Assignee: Nisshin Feed Inc., Tokyo (JP)

( * ) Notice: Subject to any disclaimer, the term of this patent is extended or adjusted under 35 U.S.C. 154(b) by 0 days.

(21) Appl. No.: 09/717,043

(22) Filed: Nov. 22, 2000

(30) Foreign Application Priority Data

Nov. 26, 1999 (JP) .............................. 11-335435

(51) Int. Cl.⁷ ..................... A23K 1/17; A61K 31/505; A61K 35/78; A01N 43/54; A01N 63/00
(52) U.S. Cl. ..................... 424/442; 514/259; 514/561; 424/769; 424/776; 424/641; 424/93.46
(58) Field of Search ................. 424/442, 769, 424/776, 641, 93.46; 514/259, 561

(56) References Cited

U.S. PATENT DOCUMENTS

| 3,941,818 | A |   | 3/1976  | Abdel-Monem |
| 4,517,178 | A | * | 5/1985  | Isono et al. |
| 5,725,894 | A | * | 3/1998  | Toyomizu et al. |
| 5,834,473 | A | * | 11/1998 | Virtanen et al. |
| 6,191,168 | B1 | * | 2/2001 | Rubenstein |

FOREIGN PATENT DOCUMENTS

| DE | 118 374     | 3/1976  |
| GB | 1 444 527   | 8/1976  |
| JP | 49-123871   | 11/1974 |
| JP | 4-178333    | 6/1992  |
| JP | 4-182433    | 6/1992  |
| JP | 4-300837    | 10/1992 |
| JP | 8-231410    | 9/1996  |
| WO | WO 94/24886 | 11/1994 |

* cited by examiner

*Primary Examiner*—Christopher R. Tate
*Assistant Examiner*—Randall Winston
(74) *Attorney, Agent, or Firm*—Oblon, Spivak, McClelland, Maier & Neustadt, P.C.

(57) ABSTRACT

Provided in this invention are a feed for animals which comprises, in addition to a cashew nut shell oil and/or anacardic acid, at least one substance selected from organic zinc compounds, betaines and microorganisms of the genus Bacillus; and a coccidiostat, which comprises, in addition to a cashew nut shell oil and/or anacardic acid, at least one substance selected from organic zinc compounds, betaines and microorganisms of the genus Bacillus.

The coccidiostat and animal feed of the present invention have excellent safety, are free from problems such as side effects, do not undergo a deterioration in their effect which otherwise occurs due to acquisition of drug resistance and exhibits high preventive or remedial effects against coccidiosis.

7 Claims, No Drawings

FEED FOR PREVENTION AND/OR TREATMENT OF COCCIDIOSIS

TECHNICAL FIELD

The present invention relates to a feed for prevention and treatment of animal coccidiosis, a coccidiostat, and a method for preventing or treating coccidiosis by supplying an animal with this feed or coccidiostat.

BACKGROUND ART

Coccidiosis of poultry such as chicken, turkey, quail and guinea fowl, domestic animals such as rabbit, cow, sheep, goat and pig, and pets such as dog and cat is a disease caused by infection with a certain kind of protozoan parasite and it is frequently found worldwide. Coccidiosis is known to be caused by, in chickens, *Eimeria tenella, Eimeria acervulina, Eimeria necatrix, Eimeria brunetti, Eimeria maxima, Eimeria mivati, Eimeria mitis, Eimeria precox* or *Eimeria hagani;* while, in turkeys, by *Eimeria meleagrimitis, Eimeria adenoides* or *Eimeria gallopovonis.*

As is apparent from the above description, species of parasitic protozoa belonging to the genus Eimeria differ between chicken and turkey. The parasitization of protozoa of the genus Eimeria is host specific. Species parasitic on chicken are not parasitic on another bird or animal, but their life cycles are much in common. Described specifically, when an animal ingests a mature oocyst with food or the like from the external world, the wall of the oocyst is broken down inside the gizzard and 4 sporocysts are liberated from one oocyst. These sporocysts are carried to the intestine, at which 2 sporozites are discharged from one sporocyst by the action of an enzyme. These two sporozoites invade the intestinal mucosa cell. By repetition of fission, sporozites each becomes a schizont embracing several to several hundreds merozites in 1 or 2 days. These merozites are released from the broken cell membrane of the schizont and penetrate through the cell of the intestinal membrane. Most of the merozites undergo sexual reproduction into microgametos (male) and macrogametos (female). They are joined and fertilized into oocysts, which are excreted into feces, dropping from the intestinal mucosa. At the time when the oocysts are discharged from the body, they are still immature and not infectious, but in several days, they become mature oocysts equipped with infectiousness. The above-described life cycle is thereafter repeated.

Animals infected with the coccidiosis-causing protozoa belonging to the genus Eimeria show symptoms such as diarrhea or bloody stool. Delay in treatment or serious symptom happens to cause death which is not so rare. Animals even escaped from the death suffer depressed growth. Coccidiosis is therefore one of the animal diseases causing a markedly serious damage and has presented a serious problem particularly for poultry raising farmers who treat a large number of domestic birds.

Upon prevention or treatment of animal coccidiosis, antibiotics (polyether antibiotics such as salinomycin), chemotherapeutics including synthetic antibacterials (such as sulfa preparation), and biological preparations such as vaccine have conventionally be employed mainly. Antibiotics and chemotherapeutics are however accompanied with such problems as emergence of side effects and deterioration of effects due to drug resistance. Vaccine, on the other hand, can be used not for treatment but only for prevention of the disease. In addition to the above-described problems, when the meat or egg of the animal to which such a drug has been administered is taken as a food, the drug residues in the animal body transfer to the human body. A severe limitation must therefore be imposed on the using amount or administration term of the drug.

There is accordingly a demand for a preventive or mitigating preparation of coccidiosis which is free of the above-described problems of an antibiotic, synthetic antibacterial or vaccine, has high safety and has an excellent anticoccidial effect. In Japanese Patent Application Laid-Open No. Hei 8-231410, proposed is a coccidiosis mitigating preparation comprising as an effective ingredient a cashew nut shell oil and/or an anacardic acid, a main component of the cashew nut shell oil. The cashew nut shell oil or anacardic acid is an oil or compound available from a cashew nut shell so that it has excellent characteristics, for example, it has high safety, is free of side effects which occur in the antibiotic or synthetic antibacterial, and furthermore, is free of a deterioration in effects due to drug resistance. A further improvement in the anticoccidial effect is however required in order to prevent or treat coccidiosis more effectively.

DISCLOSURE OF THE INVENTION

An object of the present invention is to provide a coccidiostat which has high safety, is free of problems such as side effects, is free of a decline in effects due to drug resistance and therefore exhibits high preventive and curative effects against coccidiosis; an animal feed containing it, and a method for preventing or treating animal coccidiosis by using the coccidiostat or the feed.

As a result of extensive investigation, the present inventors have found that the use of at least one substance selected from organic zinc compounds, betaines and microorganisms of the genus Bacillus in combination with the above-described cashew nut shell oil and/or an anacardic acid which has been reported to have an ameliorating effect of coccidiosis brings about an improved effect for the prevention or treatment of coccidiosis. Based on such a finding, the present invention has been completed.

The present invention therefore provides a feed for the prevention and/or treatment of coccidiosis, which comprises, together with a cashew nut shell oil and/or an anacardic acid, at least one substance selected from organic zinc compounds, betaines and microorganisms of the genus Bacillus as an effective ingredient.

The present invention also provides a coccidiostat which comprises, together with a cashew nut shell oil and/or an anacardic acid, at least one substance selected from organic zinc compounds, betaines and microorganisms of the genus Bacillus as an effective ingredient.

The present invention further provides a method for preventing or treating animal coccidiosis, which comprises administering the above-described feed or coccidiostat to an animal.

BEST MODE FOR CARRYING OUT THE INVENTION

The present invention will hereinafter be described more specifically.

The cashew nut shell oil usable in the present invention is an oil (liquid) contained in the shell of the seed of a cashew nut tree (*Anacardiumu occidentale* L.). Its preparation process is not particularly limited. As a process for preparing the cashew nut shell oil, known are, for example, a process of heating the shell separated from a cashew nut in the absence or presence of a small amount of a cashew nut shell oil to collect its oil; and a process of extracting the oil from the shell separated from a cashew nut by using an organic solvent (such as hydrocarbon solvent, ketone, alcohol or ester). In the present invention, a cashew nut oil prepared by either one of the above-described processes or a commercially available one, or a mixture thereof may be used.

The cashew nut shell oil contains cardanol, cardol, methylcardol and anacardic acids. In the present invention, anacardic acids separated and collected from the cashew nut shell oil may be used instead of the cashew nut shell oil or they may be used in combination. Anacardic acids are available by eluting the cashew nut shell oil, which has been obtained by extraction of the cashew nut shell with an organic solvent, through chromatography on a silica gel column using a solvent of n-hexane, ethyl acetate and acetic acid mixed at varied ratios (Japanese Patent Application Laid-Open No. Hei 3-240721, Japanese Patent Application Laid-Open No. Hei 3-240716, or the like).

As the organic zinc compound, those taking part in the enzymatic reaction or immune function in vivo can be used. Examples include compounds having an amino acid and zinc bonded therein and compounds having a peptide and zinc bonded therein. These organic zinc compounds may be used either singly or in combination. Specific examples of the organic zinc compound usable in the present invention include zinc-amino acid complex ("Availa-Zn", trade name; product of Zinpro Co.), zinc methionine, and a zinc methionine-zinc lysine mixture ("ZinPlex", trade name; product of Zinpro Co.).

The term "betaine" is a generic name of an internal salt having, in one molecule thereof, quaternary ammonium as a cation and in addition, an anion of an acid, particularly a carboxylic acid. As the betaine usable in the present invention, any one of such internal salts can be used. Among them, glycine betaine is preferably employed. Glycine betaine is also called lysine, oxyneurine, trimethylglycine or trimethylglycocol and it exists abundantly in many plants such as sugar radish and cotton seed. Glycine betaine separated and purified from the treacle of sucrose is ordinarily used.

Although no particular limitation is imposed on the nature of the microorganism of the genus Bacillus, *Bacillus subtilis* is preferably used.

In the present invention, it is possible to use, together with the cashew nut shell oil and/or anacardic acid, only one, any two or all three of the organic zinc compound, betaine and microorganism of the genus Bacillus. Among these, use, together with the cashew nut shell oil and/or anacardic acid, of only the microorganism of the genus Bacillus, or of the microorganism of the genus Bacillus and the organic zinc compound and/or betaine in combination tends to bring about a higher anticoccidial effect, with the combined use of the organic zinc compound, betaine and microorganism of the genus Bacillus being more effective.

The feed of the present invention can be obtained by adding, to a basal diet, at least one substance selected from organic zinc compounds, betaines and microorganisms of the genus Bacillus in addition to a cashew nut shell oil and/or an anacardic acid The content of each of the cashew nut shell oil and/or anacardic acid and at least one substance selected from organic zinc compounds, betaines and microorganisms of the genus Bacillus differs with the kind, age (month) and symptoms of the animal to be fed. From the viewpoint of an anticoccidial effect and liking of animals, it is preferred to add, based on 1000 g of a basal diet (feed prior to the addition of such components), the cashew nut shell oil and/or anacardic acid in an amount of 0.01 to 10 g (total of the cashew nut shell oil and anacardic acid when both are incorporated), particularly 1 to 5 g, the organic zinc compound in an amount of 0.005 to 0.2 g, particularly 0.02 to 0.1 g, the betaine in an amount of 0.1 to 10 g, particularly 0.2 to 1 g, the microorganism of the genus Bacillus in an amount of $10^7$ to $10^{12}$, particularly $10^8$ to $10^{10}$.

The composition of the feed of the present invention will next be described more specifically.

Preferred as the feed of the present invention are:
(i) a feed containing the organic zinc compound in an amount of 0.005 to 0.2 g, particularly 0.02 to 0.1 g in terms of Zn,
(ii) a feed containing the betaine in an amount of 0.1 to 10 g, particularly 0.2 to 1 g,
(iii) a feed containing the microorganism of the genus Bacillus in an amount of $10^7$ to $10^{12}$, particularly $10^8$ to $10^{10}$,
(iv) a feed containing the organic zinc compound in an amount of 0.05 to 0.2 g, particularly 0.02 to 0.1 g in terms of Zn, and the betaine in an amount of 0.1 to 10, particularly 0.2 to 1 g,
(v) a feed containing the organic zinc compound in an amount of 0.005 to 0.2 g, particularly 0.02 to 0.1 g in terms of Zn, and the microorganism of the genus Bacillus in an amount of $10^7$ to $10^{12}$, particularly $10^8$ to $10^{10}$,
(vi) a feed containing the betaine in an amount of 0.1 to 10 g, particularly 0.2 to 1 g and the microorganism of the genus Bacillus in an amount of $10^7$ to $10^{12}$, particularly $10^8$ to $10^{10}$, and
(vii) a feed containing the organic zinc compound in an amount of 0.005 to 0.2 g, particularly 0.02 to 0.1 g in terms of Zn, the betaine in an amount of 0.1 to 10 g, particularly 0.2 to 1 g, and the microorganism of the genus Bacillus in an amount of $10^7$ to $10^{12}$, particularly $10^8$ to $10^{10}$, in addition to the cashed nut shell oil and/or anacardic acid in an amount of 0.01 to 10 g, particularly 1 to 5 g, each based on 1000 g of the basal diet.

Among them, the feeds of (iii), (v) and (vii) containing the microorganism of the genus Bacillus, particularly the feeds of (v) and (vii) have a higher anticoccidial effect. Above all, the feed of (vii) containing, in addition to the cashew nut shell oil and/or anacardic acid, three of the organic zinc compound, betaine and microorganism of the genus Bacillus in the above-described predetermined amounts, respectively exhibits a markedly high anticoccidial effect.

There is no particular limitation imposed on the kind or amount of the components contained in the basal diet insofar as they are conventionally fed to animals. For example, corn, corn powder, milo, soybean meal, oats, wheat short, wheat crude powder, alfalfa, clover, defatted rice bran, fish meal, yeast, treacle, meat piece, bone meal, calcium carbonate, calcium diphosphate, yellow grease, vitamins and/or minerals may be added as needed.

The coccidiostat according to the present invention is available by mixing, with the cashew nut shell oil and/or anacardic acid, at least one substance selected from organic zinc compounds, betaines and microorganisms of the genus Bacillus.

An amount of each of the components of the coccidiostat of the present invention can be adjusted, depending on the kind, age (month) or symptoms of the animal to be fed. From the viewpoint of an anticoccidial effect, however, it is preferred to add, relative to 1 g of the cashew nut shell oil and/or anacardic acid (total amount when both of the cashew nut shell oil and anacardic acid are contained),
(i) the organic zinc compound in an amount of 0.005 to 0.1 g, particularly 0.01 to 0.03 g in terms of Zn,
(ii) the betaine in an amount of 0.05 to 5 g, particularly 0.1 to 0.5 g, (iii) the microorganism of the genus Bacillus in an amount of $10^7$ to $10^{12}$, particularly $10^8$ to $10^{10}$, (iv) the organic zinc compound in an amount of 0.005 to 0.1 g, particularly 0.01 to 0.03 g in terms of Zn, and the betaine in an amount of 0.05 to 5 g, particularly 0.1 to 0.5 g, (v) the organic zinc compound in an amount of 0.005 to 0.1 g, particularly 0.01 to 0.03 g in terms of Zn and the microorganism of the genus Bacillus in an amount of $10^7$ to $10^{12}$, particularly $10^8$ to $10^{10}$, (vi) the betaine in an amount of 0.05 to 5 g, particularly 0.1 to 0.5 g and the microorganism of the genus Bacillus in an amount of $10^7$ to $10^{12}$, particularly $10^8$ to $10^{10}$, or (vii) the organic zinc compound in an amount of 0.005 to 0.1 g, particularly 0.01 to 0.03 g in terms of Zn, the betaine in an amount of 0.05 to 5 g, particularly 0.1 to 0.5 g, and the microorganism of the genus Bacillus in an amount of $10^7$ to $10^{12}$, particularly $10^8$ to $10^{10}$.

The coccidiostat according to the present invention may be supplied in any form such as liquid, semisolid (paste or the like) or solid. As a solid form, it can be formulated into powders, granules, tablets, capsules or pills.

The coccidiostat of the present invention can contain various components ordinarily added to a drug such as excipient, filler, binder, disintegrator, sweetener, flavor and spice.

Upon administration of the coccidiostat of the present invention to animals, either oral administration or parenteral administration can be employed, but oral administration is preferred. It may be administered directly to animals or after addition to a feed for animals.

The feed or coccidiostat of the present invention can be used for the prevention or treatment of coccidiosis of not only poultry such as chicken, turkey, quail, geese and guinea fowl, livestock such as pig, cow, sheep, goat and rabbit, and pets such as dog and cat but also any animal known to be infected with coccidiosis.

The amount of the feed or coccidiostat of the present invention to be added to an animal differs with the kind or age (month) of the animal or feeding method thereto. Upon oral administration to a chicken, it is usually recommended to feed the cashew nut shell oil and/or anacardic acid in an amount of about 0.1 to 0.3 g/kg in weight/day; the organic zinc compound in an amount of about 1 to 10 mg/kg in weight/day in terms of Zn; and/or the microorganism of the genus Bacillus in an amount of about $10^6$ to $10^9$/weight kg/day for several days to several tens day.

The feed or coccidiostat of the present invention may be administered to an animal throughout its breeding period or during a certain period. In particular, feeding from just after the birth until 5 weeks of age brings about a high anticoccidial effect.

EXAMPLES

The present invention will hereinafter be described in detail by Examples. It should however be borne in mind that the present invention is not limited to or by them.

Example 1

(1) A mixed feed (basal diet) having the composition as described below in Table 1 and being free from an antibiotic and a synthetic coccidiostat was prepared for the first stage of a broiler.

TABLE 1

Composition of feed (basal diet) for the first stage of broiler

| corn | 400 parts by weight |
|---|---|
| milo | 200 parts by weight |
| Soybean meal | 160 parts by weight |
| defatted rice bran | 49 parts by weight |
| Fish meal | 160 parts by weight |
| calcium carbonate | 8 parts by weight |
| yellow grease | 16 parts by weight |
| salt | 2 parts by weight |
| vitamin mix | 2 parts by weight |
| methionine | 1 part by weight |
| mineral mix | 2 parts by weight |
| total | 1000 parts by weight |

(2) Ten one-day-old Chunkey (male) chicks were prepared in each of 11 plots (Test lot 1 to Test lot 11). (110 chickens in total).

(3) The basal diet as described in Table 1 was fed as was to the chicks in Test lot 1. Without infection with *Eimeria tenella,* they were fed up to 17 days of age with the feed and water ad libitum. At 17 days of age, they were dissected.

(4) The chicks in Test lots 2 to 11 were each fed ad libitum with the above-described basal diet in Table 1 or one of the below-described feeds in Table 2 obtained by adding the component(s) to the basal diet, together with water. On 9 days of age, oral infection with 10000 oocysts/chick of *Eimeria tenella* was conducted. They were fed up to 17 days of age and were dissected at 17 days of age.

The amount of each component in Table 2 is based on the weight of the basal diet (outer percentage).

TABLE 2

| Test lot | Contents of feed[1] |
|---|---|
| Lots 1 & 12 | Basal diet (not infected) |
| Lots 2 & 13 | Basal diet |
| Lots 3 & 14 | Basal diet + 0.2% of cashew nut shell oil |
| Lots 4 & 15 | Basal diet + 40 ppm of organic zinc compound[2] |
| Lots 5 & 16 | Basal diet + 0.05% of betaine[3] |
| Lots 6 & 17 | Basal diet + $10^5$/g of *Bacillus subtilis* |
| Lots 7 & 18 | Basal diet + 0.2% of cashew nut shell oil + 40 ppm of organic zinc compound[2] |
| Lots 8 & 19 | Basal diet + 0.2% of cashew nut shell oil + 0.05% of betaine[3] |
| Lots 9 & 20 | Basal diet + 0.2% of cashew nut shell oil + $10^5$/g of *Bacillus subtilis*[4] |
| Lots 10 & 21 | Basal diet + 0.2% of cashew nut shell oil + 40 ppm of organic zinc compound[2] + $10^5$/g of *Bacillus subtilis*[4] |
| Lots 11 & 22 | Basal diet + 50 ppm of salinomycin |

[1] Amount of each component added is based on the weight of the basal diet.
[2] A zinc - amino acid complex ["Availa-zn", product of ZINPRO CORPORATION; zinc content: 10%)
[3] glycine betaine [product of FINNFEED (Finland)]
[4] "CALSPORIN", product of CALPIS Co., Ltd. (amount per g of the basal diet)

(5) In each plot, a mean weight upon initiation of breeding, a mean weight upon completion of breeding (17 days of age), a mean intake amount (mean feed intake amount) per chick for a breeding period (17 days) were measured and based on them, a mean weight increase and a mean weight-increasing ratio (a ratio of a mean weight increase in Test plots 2 to 11 to an average weight increase in Test plot 1 free of infection with *Eimeria tenella* designated as 100) were determined. The results are as shown below in Tables 5 and 6.

In each of Test plots 1 to 11, the survival ratio of the chicks on 17 days of age was 100% as shown in Tables 5 and 6.

(6) In each plot, feces were collected from a fecal plate on the dissection day and the number of oocysts of *Eimeria tenella* in 1 g of the feces was counted. The results are as shown in Tables 5 and 6.

(7) The presence or absence, and conditions of the lesion in the cecum of the dissected chick was evaluated in accordance with the judging criteria as shown below in Table 3. Evaluation was conducted by scores (in terms of point), with − as 0, + as 1, ++ as 2, +++ as 3 and ++++ as 4. The total point of each test plot was determined and it was divided by 10 to determine a mean lesion value. The results are as shown in Tables 5 and 6.

TABLE 3

| Symbol | Score | Details |
|---|---|---|
| − | 0 | Utterly normal cecum. |
| + | 1 | Normal in cecum shape. Cecum contents have a little fluidity and are yellowish. Cecum mucosa has, in part, light swelling and is whitish. |
| ++ | 2 | Almost normal in cecum shape. Swelling is observed in the whole mucosa. Contents are free from hemorrhage and mucus is yellowish and faded. A small number of white necrosis or hemorrhage spots are observed in the mucosa. |
| +++ | 3 | Cecum has apparent atrophy or deformation and is a little longer than rectum. Cecum contains no normal contents and is filled with coagulated or grayish white cheese-like modified contents. |

TABLE 3-continued

| Symbol | Score | Details |
|---|---|---|
| | | Thickening of cecum wall is apparent and the wall is fragile. Hemorrhage spots have remained in it. Lesion reaches even cecum base but does not reach rectum. |
| ++++ | 4 | Cecum atrophy or deformation is marked. Cecum becomes a sausage-like shape and the length is equal or shorter than that of rectum. Lesion reaches at the ⅓ to ¼ of the rectum. |

(8) The number of oocysts per g of the cecum of the dissected chick was measured and evaluated in accordance with the criteria as shown below in Table 4. The results are as shown in Tables 5 and 6.

TABLE 4

| Symbol | The number of oocysts |
|---|---|
| − | 0 or greater but less than $1.0 \times 10^5$ |
| + | $1.0 \times 10^5$ or greater but less than $2.0 \times 10^6$ |
| ++ | $2.0 \times 10^6$ or greater but less than $6.0 \times 10^6$ |
| +++ | $6.0 \times 10^6$ or greater but less than $1.0 \times 10^7$ |
| ++++ | $1.0 \times 10^7$ or greater |

TABLE 5

| | Lot 1 (not infected) | Lot 2 (control) | Lot 3 (comparative Example) | Lot 4 (comparative Example) | Lot 5 (Comparative Example) | Lot 6 (comparative Example) |
|---|---|---|---|---|---|---|
| Mean weight (g) upon initiation | 155 ± 13 | 155 ± 10 | 155 ± 15 | 155 ± 15 | 155 ± 13 | 155 ± 10 |
| Mean weight (g) upon completion | 515 ± 38 | 476 ± 47 | 479 ± 35 | 479 ± 35 | 482 ± 24 | 490 ± 68 |
| Weight increase (g) during breeding | 360 | 321 | 332 | 324 | 327 | 335 |
| Weight increase ratio | 100.0 | 89.2 | 92.2 | 90.0 | 90.8 | 93.1 |
| Mean feed intake (g) | 450 | 424 | 425 | 421 | 422 | 439 |
| Feed demand ratio | 1.25 | 1.32 | 1.28 | 1.30 | 1.29 | 1.31 |
| Survival ratio (%) | 100 | 100 | 100 | 100 | 100 | 100 |
| The number of oocysts in feces (/g) | 0 | $450 \times 10^3$ | $320 \times 10^3$ | $372 \times 10^3$ | $204 \times 10^3$ | $150 \times 10^3$ |
| Cecum lesion | | | | | | |
| − (0) | 10 | | | | | |
| + (1) | | | 3 | 1 | 1 | 1 |
| ++ (2) | | 4 | 5 | 3 | 3 | 5 |
| +++ (3) | | 4 | 2 | 3 | 5 | 4 |
| ++++ (4) | | 2 | | 3 | 1 | |
| Average lesion value | 0.0 | 2.8 ± 0.8 | 1.9 ± 0.7 | 2.8 ± 1.0 | 2.6 ± 0.8 | 2.3 ± 0.7 |
| The number of oocysts in cecum | | | | | | |
| − | 10 | | | | 1 | |
| + | | | 1 | 1 | | 1 |
| ++ | | 4 | 5 | 1 | 6 | 4 |
| +++ | | 4 | 2 | 4 | 3 | 5 |
| ++++ | | 2 | 2 | 4 | | |

TABLE 6

|  | Lot 7 (Example) | Lot 8 (Example) | Lot 9 (Example) | Lot 10 (Example) | Lot 11 (Referential Example) |
|---|---|---|---|---|---|
| Mean weight (g) upon initiation | 155 ± 14 | 155 ± 9 | 155 ± 10 | 155 ± 13 | 155 ± 18 |
| Mean weight (g) upon completion | 483 ± 43 | 490 ± 46 | 493 ± 50 | 501 ± 31 | 462 ± 68 |
| Weight increase (g) during breeding | 328 | 335 | 338 | 346 | 338 |
| Weight increase ratio | 91.1 | 93.1 | 93.9 | 96.1 | 93.9 |
| Mean feed intake (g) | 417 | 425 | 433 | 443 | 433 |
| Feed demand ratio | 1.27 | 1.27 | 1.28 | 1.28 | 1.28 |
| Survival ratio (%) | 100 | 100 | 100 | 100 | 100 |
| The number of oocysts in feces (g) | $270 \times 10^3$ | $300 \times 10^3$ | $124 \times 10^3$ | $100 \times 10^3$ | $46 \times 10^3$ |
| Cecum lesion |  |  |  |  |  |
| − (0) | 5 | 4 | 6 | 7 | 8 |
| + (1) | 2 | 3 | 4 | 2 | 1 |
| ++ (2) | 2 | 3 |  | 1 | 1 |
| +++ (3) | 1 |  | 1 |  |  |
| ++++ (4) |  |  |  |  |  |
| Average lesion value | 0.9 ± 1.1* | 0.9 ± 0.9* | 0.7 ± 0.9* | 0.4 ± 0.7* | 0.3 ± 0.7 |
| The number of oocysts in cecum |  |  |  |  |  |
| − |  | 1 | 1 | 1 | 1 |
| + | 2 | 2 | 2 | 2 | 4 |
| ++ | 3 | 2 | 2 | 2 | 4 |
| +++ | 4 | 4 | 4 | 3 | 2 |
| ++++ | 1 | 1 |  |  | 1 |

*Significant difference from Lot 3 ($P < 0.05$)

From the above-described results in Tables 5 and 6, it has been understood that in Lots 7 to 10 wherein a feed containing, in addition to a cashew nut shell oil, at least one substance selected from organic zinc compounds, betaines and microorganisms of the genus Bacillus, the mean lesion value in the cecum is low, suggesting that infection with *Eimeria tenella* is suppressed to a low level. Particularly in Lots 9 and 10 wherein a feed contains a cashew nut shell oil and a microorganism of the genus Bacillus, the average lesion value is suppressed to a still lower level.

Example 2

(1) Ten one-day-old Chunkey (male) chicks were prepared in each of 11 plots (Test lot 12 to Test lot 22). (110 chicks in total)

(2) The basal diet as described in Table 1 was fed as was to the chicks in Test lot 12. Without infection with *Eimeria acervulina*, they were fed up to 15 days of age with the feed and drinking water ad libitum. At 15 days of age, they were dissected.

(3) The chicks in Test lots 13 to 22 were each fed with the feeds as shown in Table 2 ad libitum, together with drinking water. On 9 days of age, oral infection with 10000 oocysts/chicken of *Eimeria acervulina* was conducted. They were fed up to 15 days of age and were dissected at 17 days of age.

(4) In each plot, a mean weight upon initiation of breeding, a mean weight upon completion of breeding (17 days of age), a mean intake amount (mean feed intake amount) per chick for a breeding period (15 days) were measured and based on them, a mean weight increase and a mean weight-increasing ratio (a ratio of a mean weight increase in Test plots 12 to 22 to an average weight increase in Test plot 1 free of infection with *Eimeria acervulina*, which was designated as 100) were determined. The results are as shown in Tables 8 and 9. In each of Test plots 12 to 22, the survival ratio of the chicks on 15 days of age was 100% as shown in Tables 8 and 9.

(5) In each plot, feces were collected from the fecal plate on the dissection day and the number of oocysts of *Eimeria acervulina* in 1 g of the feces was counted. The results are as shown in Tables 8 and 9.

(6) The presence or absence, and conditions of the lesion in the small intestine of the dissected chick was evaluated in accordance with the judging criteria as shown below in Table 7. Evaluation was conducted by scores (in terms of points), with − as 0, + as 1, ++ as 2, +++ as 3 and ++++ as 4. The total point of each test plot was determined and it was divided by 10 to determine a mean lesion value. The results are as shown in Tables 8 and 9.

(7) The number of oocysts per g of the small intestine of the dissected chick was measured and evaluated based on the above-described criteria in Table 4. The results are as shown in Tables 8 and 9.

TABLE 7

| Symbol | Score | Details |
|---|---|---|
| − | 0 | Small intestine is utterly normal. |
| + | 1 | Several white necrosis lesions irregular in shape are observed at the duodenum and upper part of the small intestine. |
| ++ | 2 | Necrosis lesions (mainly, colonies of oocysts) are scattered at the duodenum and upper part of the small intestine. |
| +++ | 3 | A number of necrosis lesions are observed at the duodenum and upper part of the small intestine. The intestine contains a mucus. These necrosis lesions sometimes reach even the middle part of the small intestine. |
| ++++ | 4 | Lesions exist innumerably. They are combined each other at the upper part of the small intestine and the whole small intestine assumes a grayish white color. Contents of the small intestine contain a mucus abundantly, and cheese-like modified substances happen to stick to the epedermis of the small intestine. |

TABLE 8

|  | Lot 12 (not infected) | Lot 13 (Control) | Lot 14 (Comparative Example) | Lot 15 (Comparative Example) | Lot 16 (Comparative Example) | Lot 17 (Comparative Example) |
|---|---|---|---|---|---|---|
| Mean weight (g) upon initiation | 155 ± 13 | 155 ± 10 | 155 ± 15 | 155 ± 12 | 155 ± 11 | 155 ± 12 |
| Mean weight (g) upon completion | 418 ± 30 | 381 ± 26 | 397 ± 35 | 389 ± 36 | 386 ± 30 | 399 ± 28 |
| Weight increase (g) during bleeding | 263 | 226 | 252 | 234 | 231 | 244 |
| Weight increase ratio | 100.0 | 85.9 | 92.0 | 89.0 | 87.8 | 92.8 |
| Mean feed intake (g) | 331 | 294 | 312 | 300 | 293 | 315 |
| Feed demand ratio | 1.26 | 1.30 | 1.29 | 1.28 | 1.27 | 1.29 |
| Survival ratio (%) | 100 | 100 | 100 | 100 | 100 | 100 |
| The number of oocysts in feces (/g) | 0 | 2244 × $10^3$ | 3728 × $10^3$ | 1792 × $10^3$ | 27884 × $10^3$ | 1567 × $10^3$ |
| Small intestine lesion |  |  |  |  |  |  |
| − (0) | 10 |  |  |  |  |  |
| + (1) |  |  | 2 | 2 | 1 | 2 |
| ++ (2) |  | 4 | 4 | 3 | 2 | 3 |
| +++ (3) |  | 3 | 4 | 3 | 6 | 3 |
| ++++ (4) |  | 3 | 3 | 2 | 1 | 2 |
| Average lesion value | 0.0 | 2.9 ± 0.9 | 2.2 ± 0.8 | 2.5 ± 1.1 | 2.7 ± 0.8 | 2.5 ± 1.1 |
| The number of oocysts in small intestine |  |  |  |  |  |  |
| − | 10 |  |  | 2 | 1 |  |
| + |  |  | 4 | 3 | 6 | 2 |
| ++ |  | 6 | 4 | 3 | 2 | 6 |
| +++ |  | 3 | 2 | 2 | 1 | 2 |
| ++++ |  | 1 |  |  |  |  |

TABLE 9

|  | Lot 18 (Example) | Lot 19 (Example) | Lot 20 (Example) | Lot 21 (Example) | Lot 22 (Example) |
|---|---|---|---|---|---|
| Mean weight (g) upon initiation | 155 ± 14 | 155 ± 10 | 155 ± 13 | 155 ± 15 | 155 ± 10 |
| Mean weight (g) upon completion | 400 ± 31 | 304 ± 33 | 402 ± 30 | 407 ± 28 | 410 ± 31 |

TABLE 9-continued

|  | Lot 18 (Example) | Lot 19 (Example) | Lot 20 (Example) | Lot 21 (Example) | Lot 22 (Example) |
| --- | --- | --- | --- | --- | --- |
| Weight increase (g) during breeding | 245 | 250 | 247 | 252 | 255 |
| Weight increase ratio | 93.2 | 95.1 | 93.9 | 95.8 | 97.0 |
| Mean feed intake (g) | 314 | 323 | 319 | 320 | 326 |
| Feed demand ratio | 1.28 | 1.29 | 1.29 | 1.27 | 1.28 |
| Survival ratio (%) | 100 | 100 | 100 | 100 | 100 |
| The number of oocysts in feces (/g) | $1356 \times 10^3$ | $1404 \times 10^3$ | $1245 \times 10^3$ | $1124 \times 10^3$ | $404 \times 10^3$ |
| Cecum lesion |  |  |  |  |  |
| − (0) | 2 | 3 | 2 | 6 | 7 |
| + (1) | 5 | 4 | 4 | 3 | 3 |
| ++ (2) | 2 | 2 | 4 | 1 |  |
| +++ (3) | 1 | 1 |  |  |  |
| ++++ (4) |  |  |  |  |  |
| Average lesion value | 1.2 ± 0.9* | 1.1 ± 1.0* | 1.2 ± 0.8* | 0.5 ± 0.7* | 0.3 ± 0.7* |
| The number of oocysts in cecum |  |  |  |  |  |
| − |  | 1 | 2 | 1 | 1 | 3 |
| + | 4 | 4 | 3 | 4 | 3 |
| ++ | 3 | 2 | 4 | 5 | 3 |
| +++ | 2 | 2 | 2 |  | 1 |
| ++++ | 1 | 1 |  |  |  |

*Significant difference from Lot 3 (P < 0.05)

From the above-described results shown in Tables 8 and 9, it has been understood that in Lots 18 to 21 wherein a feed containing, in addition to a cashew nut shell oil, at least one substance selected from organic zinc compounds, betaines and microorganisms of the genus Bacillus, the mean lesion value in the small intestine is low, suggesting that infection with *Eimeria acervulina* is suppressed to a low level. Particularly in Lot 21 wherein a feed contains, in addition to a cashew nut shell oil, an organic zinc compound, betaine and microorganism of the genus Bacillus, the average lesion value is suppressed to a still lower level.

Capability of Exploitation in Industry

The feed and coccidiostat according to the present invention are free from emergence of such side effects as caused by an antibiotic or chemotherapeutic or a decline in effects due to acquisition of drug resistance and can therefore be used safely and effectively for the prevention and treatment of coccidiosis of various animals. When it is administered to the animal infected with coccidiosis, it can ameliorate the symptoms.

The feed or coccidiostat of the present invention is particularly effective against coccidiosis of domestic birds and can therefore lighten the burden of poultry farmers who treat a large number of domestic birds.

Since the cashew nut shell oil serving as an effective ingredient of the coccidiostat of the present invention is available from the shell of a cashew nut, while the anarcadic acid is available from its oil, they are safe.

In addition to the preventive or remedial effects against coccidiosis of animals, the feed or coccidiostat of the present invention is effective for improving the growth of the animals to be fed therewith.

What is claimed is:

1. A feed for the prevention and/or treatment of coccidiosis which comprises, an effective amount of cashew nut shell oil and/or anacardic acid and an effective amount of at least one substance selected from the group consisting of organic zinc compounds and microorganisms of the genus Bacillus, wherein said organic zinc compound is at least one compound selected from the group consisting of compounds having an amino acid and zinc bonded therein and compounds having a peptide and zinc bonded therein and said microorganism of the genus Bacillus is *Bacillus subtilis*.

2. A feed for the prevention and/or treatment of coccidiosis which comprises, an effective amount of cashew nut shell oil and/or anacardic acid and an effective amount of at least one substance selected from the group consisting of organic zinc compounds, betaines and microorganisms of the genus Bacillus, wherein said cashew nut shell oil and/or anacardic acid is contained in an amount of 0.01 to 10 g based on 1000 g of said feed; and (i) said organic zinc compound is contained in an amount of 0.005 to 0.2 g in terms of Zn, (ii) said betaine is contained in an amount of 0.1 to 10 g, (iii) said microorganism of the genus Bacillus is contained in an amount of $10^7$ to $10^{12}$, (iv) said organic zinc compound is contained in an amount of 0.005 to 0.2 g in terms of Zn and said betaine is contained in an amount of 0.1 to 10 g, (v) said organic zinc compound is contained in an amount of 0.005 to 0.2 g in terms of Zn and said microorganism of the genus Bacillus is contained in an amount of $10^7$ to $10^{12}$, (vi) said betaine is contained in an amount of 0.1 to 10 g and said microorganism of the genus Bacillus is contained in an amount of $10^7$ to $10^{12}$, or (vii) said organic zinc compound is contained in an amount of 0.005 to 0.2 g in terms of Zn, said betaine is contained in an amount of 0.1 to 10 g and said microorganism of the genus Bacillus is contained in an amount of $10^7$ to $10^{12}$.

3. A coccidiostat which comprises, an effective amount of a cashew nut shell oil and/or anacardic acid and an effective amount of at least one substance selected from the group consisting of organic zinc compounds and microorganisms of the genus Bacillus, wherein said organic zinc compound is at least one compound selected from the group consisting of compounds having an amino acid and zinc bonded therein and compounds having a peptide and zinc bonded therein and said microorganism of the genus Bacillus is *Bacillus subtilis*.

4. A feed for the prevention and/or treatment of coccidiosis which comprises an effective amount of cashew nut shell oil and/or anacardic acid and an effective amount of at least one substance selected from the group consisting of organic zinc compounds, betaines and microorganisms of the genus Bacillus, wherein relative to 1 g of said cashew nut shell oil and/or anacardic acid, (i) said organic zinc compound is contained in an amount of 0.005 to 0.1 g in terms of Zn, (ii) said betaine is contained in an amount of 0.05 to 5 g, (iii) said microorganism of the genus Bacillus is contained in an amount of $10^7$ to $10^{12}$, (iv) said organic zinc compound is contained in an amount of 0.005 to. 0.1 g in terms of Zn, and said betaine is contained in an amount of 0.05 to 5 g, (v) said organic zinc compound is contained in an amount of 0.005 to 0.1 g in terms of Zn and said microorganism of the genus Bacillus is contained in an amount of $10^7$ to $10^{12}$, (vi) said betaine is contained in an amount of 0.05 to 5 g and the microorganism of said genus Bacillus is contained in an amount of $10^7$ to $10^{12}$, or (vii) said organic zinc compound is contained in an amount of 0.005 to 0.1 g in terms of Zn, said betaine is contained in an amount of 0.05 to 5 g, and said microorganism of the genus Bacillus is contained in an amount of $10^7$ to $10^{12}$.

5. A method for preventing or treating coccidiosis of an animal, which comprises feeding the animal with any one of the feeds as claimed in any one of claim 1, 2, or 4, or the coccidiostat as claimed in claim 4.

6. A feed for the prevention and/or treatment of coccidiosis which comprises, an effective amount of cashew nut shell oil and/or anacardic acid and an effective amount of at least one substance selected from the group consisting of organic zinc compounds, betaines and microorganisms of the genus Bacillus, wherein said cashew nut shell oil and/or anacardic acid is contained in an amount of 1 to 5 g based on 1000 g of said feed; and (i) said organic zinc compound is contained in an amount of 0.02 to 0.1 g in terms of Zn, (ii) said betaine is contained in an amount of 0.2 to 1 g, (iii) said microorganism of the genus Bacillus is contained in an amount of $10^8$ to $10^{10}$, (iv) said organic zinc compound is contained in an amount of 0.02 to 0.1 g in terms of Zn and the betaine is contained in an amount of 0.2 to 1 g, (v) said organic zinc compound is contained in an amount of 0.02 to 0.1 g in terms of Zn and said microorganism of the genus Bacillus is contained in an amount of $10^8$ to $10^{10}$, (vi) said betaine is contained in an amount of 0.2 to 1 g and the microorganism of the genus Bacillus is contained in an amount of $10^8$ to $10^{10}$, or (vii) the organic zinc compound is contained in an amount of 0.02 to 0.1 g in terms of Zn, the betaine is contained in an amount of 0.2 to 1 g and the microorganism of the genus Bacillus is contained in an amount of $10^8$ to $10^{10}$.

7. A coccidiostat which comprises, a cashew nut shell oil and/or anacardic acid and an effective amount of at least one substance selected from the group consisting of organic zinc compounds, betaines and microorganisms of the genus Bacillus, wherein relative to 1 g of said cashew nut shell oil and/or anacardic acid, (i) said organic zinc compound is contained in an amount of 0.01 to 0.03 g in terms of Zn, (ii) said betaine is contained in an amount of 0.01 to 0.5 g, (iii) said microorganism of the genus Bacillus is contained in an amount of $10^8$ to $10^{10}$, (iv) said organic zinc compound is contained in an amount of 0.01 to 0.03 g in terms of Zn, and said betaine is contained in an amount of 0.1 to 0.5 g, (v) said organic zinc compound is contained in an amount of 0.01 to 0.03 g in terms of Zn and said microorganism of the genus Bacillus is contained in an amount of $10^8$ to $10^{10}$, (vi) said betaine is contained in an amount of 0.1 to 0.5 g and said microorganism of the genus Bacillus is contained in an amount of $10^8$ to $10^{10}$, or (vii) said organic zinc compound is contained in an amount of 0.01 to 0.03 g in terms of Zn, said betaine is contained in an amount of 0.1 to 0.5 g, and said microorganism of the genus Bacillus is contained in an amount of $10^8$ to $10^{10}$.

* * * * *

UNITED STATES PATENT AND TRADEMARK OFFICE
CERTIFICATE OF CORRECTION

PATENT NO. : 6,379,694 B1
DATED : April 30, 2002
INVENTOR(S) : Kazuhiro Hatano et al.

It is certified that error appears in the above-identified patent and that said Letters Patent is hereby corrected as shown below:

<u>Column 15,</u>
Line 30, "claim 4" should read -- claim 3 --.

Signed and Sealed this

First Day of October, 2002

*Attest:*

*Attesting Officer*

JAMES E. ROGAN
*Director of the United States Patent and Trademark Office*